US005496360A

United States Patent [19]
Hoffmann et al.

[11] Patent Number: 5,496,360
[45] Date of Patent: Mar. 5, 1996

[54] IMPLANTABLE CARDIAC ELECTRODE WITH RATE CONTROLLED DRUG DELIVERY

[75] Inventors: Drew A. Hoffmann, Los Gatos; M. Elizabeth Bush, Fremont, both of Calif.

[73] Assignee: Ventritex, Inc., Sunnyvale, Calif.

[21] Appl. No.: 226,594

[22] Filed: Apr. 12, 1994

[51] Int. Cl.$^6$ ..................................................... A61N 1/04
[52] U.S. Cl. .......................... 607/120; 128/642; 607/122
[58] Field of Search ............................ 604/890.1, 891.1, 604/892.1; 607/120

[56] References Cited

U.S. PATENT DOCUMENTS

| | | | |
|---|---|---|---|
| 4,506,680 | 3/1985 | Stokes | 128/786 |
| 4,577,642 | 3/1986 | Stokes | 128/784 |
| 4,606,118 | 8/1986 | Cannon et al. | 29/825 |
| 4,711,251 | 12/1987 | Stokes | 128/784 |
| 4,819,661 | 4/1989 | Heil, Jr. et al. | 128/786 |
| 4,819,662 | 4/1989 | Heil, Jr. et al. | 128/786 |
| 4,844,099 | 7/1989 | Skalsky et al. | 128/785 |
| 4,922,926 | 5/1990 | Hirschberg et al. | 128/785 |
| 4,940,465 | 7/1990 | Theeuwes et al. | 604/892.1 |
| 4,953,564 | 9/1990 | Berthelsen | 128/784 |
| 4,960,416 | 10/1990 | Stephens et al. | 604/892.1 |
| 4,972,848 | 11/1990 | Di Domenico et al. | 128/785 |
| 4,976,966 | 12/1990 | Theeuwes et al. | 604/892.1 |
| 5,002,067 | 3/1991 | Berthelsen et al. | 128/786 |
| 5,020,544 | 6/1991 | Dahl et al. | 128/784 |
| 5,030,448 | 7/1991 | Hunter | 424/83 |
| 5,098,425 | 3/1992 | Eckenhoff | 604/892.1 |
| 5,103,837 | 4/1992 | Weidlich et al. | 128/784 |
| 5,108,756 | 4/1992 | Curatolo | 604/892.1 |
| 5,154,182 | 10/1992 | Moaddeb | 128/784 |
| 5,221,278 | 6/1993 | Linkwitz et al. | 604/892.1 |
| 5,226,902 | 7/1993 | Bae et al. | 604/892.1 |
| 5,229,133 | 7/1993 | Wright et al. | 604/892.1 |
| 5,234,424 | 8/1993 | Yum et al. | 604/892.1 |
| 5,320,616 | 6/1994 | Magruder et al. | 604/892.1 |
| 5,324,280 | 6/1994 | Wong et al. | 604/892.1 |

OTHER PUBLICATIONS

"In Vivi–In Vitro Correlation of Salbutamol Release from a Controlled Release Osmotic Pump Delivery System", Civiale, C., et al., Methods and Findings in Experimental and Clinical Pharmacology, vol. 13, No. 7, 1991 pp. 491–498.

"Calcium Antagonists in Cardiology: Update on Sustained–Release Drug Delivery Systems", Michelson, E. L., Clin. Cardiol. 14, 1991, pp. 947–950.

"Magnetic Resonance Imaging of the Delivery of a Paramagnetic Contrast Agent by an Osmotic Pump", Carpenter, T. A., et al., Drug Design and Delivery, 1988, vol. 3, pp. 263–266.

"Therapeutic Effects of Local Delivery of Dexamethasone on Experimental Brain tumors and Peritumoral Brain Edema", Ikeda, Y., et al., J. Nuerosurg. vol. 79, Nov. 1993, pp. 716–721.

"Prolongation of Heterotopic Heart Allograft Survival by Local Delivery of Continuous Low–Dose Cyclosporine therapy", Stepkowski, S. M., et al., Transplantation, vol. 47, No. 1, Jan. 1989, pp. 17–23.

"The Electrode–Tissue Interface: The Revolutionary Role of Steriod Elution", Mond, H. G., et al., PACE, vol. 15, Jan. 1992, pp. 95–107.

(List continued on next page.)

*Primary Examiner*—William E. Kamm
*Assistant Examiner*—Marianne Parker
*Attorney, Agent, or Firm*—M. Elizabeth Bush; Steven M. Mitchell; Mark J. Meltzer

[57] ABSTRACT

A body implantable electrode with rate controlled drug delivery is disclosed. A body implantable lead is provided for the delivery of stimulation energy to a desired body site includes a drug dispenser carried by the lead which retains a drug to be dispensed at least adjacent the desired body stimulation site. The drug may be one which is intended to counter thrombus formation, fibrosis, inflammation or arrhythmias, for example. The drug may be in liquid or powder form retained in a reservoir carried by the lead. The reservoir is formed as a pump which controls dispensing of the drug using a fluid drawing agent such as a salt.

28 Claims, 12 Drawing Sheets

OTHER PUBLICATIONS

"The Osmotic Pump: Novel Research Tool for Optimizing Drug Regimens", Echenhoff, B., et al., Biomaterials, vol. 2, Apr. 1981, pp. 89–96.

"Nifedipine Gastrointestinal Therapeutic System", Swanson, D. R., et al., The American Journal of Medicine, vol. 83 (Suppl. 6B), Dec. 21, 1987, pp. 3–9.

"Drug Delivery Systems 4. Implants in Drug Delivery", Ranade, V. V., J. Clin. Pharmacol, 1990;30:871–889.

"Mechanical Deformation of Polymer Matrix Controlled Release Devices Modulates Drug Release" Edelman, E. R., et al, Journal of Biomedical Materials Research, vol. 26, 1992, pp. 1619–1631.

"Initial Screening of Bio–Active Agents with Potential to Reduce Stimulation Threshold", Brewer, G., et al., PACE, vol. 11, Apr. 1988, pp. 509 #105.

"The Electrode–Biointerface: Stimulation" Stokes, K. et al., Modern Cardiac Pacing, edited by S. Serge Barold, MD., Futura Publishing Co., 1985, pp. 33–77.

"Strong Buffering Characteristics and Swelling Behavior of Cationic Copolymers" Nikolaos A. Peppas, et al., Journal of Applied Polymer Science, vol. 52, (1994) pp. 763–768.

"Measuremnt of the Swelling Force in Ionic Polymeric Networks. I. Effect of pH and Ionic Content" Atul R. Khare, et al., Journal of Controlled Release, 22 (1992) pp 239–244.

IMPLANTABLE CARDIAC ELECTRODE WITH RATE CONTROLLED DRUG DELIVERY

FIELD OF THE INVENTION

This invention relates to implantable cardiac electrodes in general, and more particularly to such electrodes having means for controllably releasing a drug or steroid at the site of implantation of the electrode.

BACKGROUND OF THE INVENTION

The use of steroids and drugs released in vivo to counter trauma caused by an implanted device such as a cardiac pacemaker lead is well known. Such trauma typically occurs in the region of attachment of the distal end of the pacing lead to the cardiac tissue.

Tined pacing leads which have a cavity or collar at the distal end of the lead containing a drug to counter undesirable interactions between the lead and tissue are disclosed in U.S. Pat. Nos. 4,711,251 and 4,506,680, to Stokes, U.S. Pat. No. 4,844,099, to Skalsky et al., and U.S. Pat. No. 4,972,848, to Di Domenico et al. The drug of Di Domenico et al. is compounded within a polymer matrix specifically chosen to be dimensionally stable, not expanding when hydrated. They suggest that the degree of crosslinking of the polymer may be useful in varying the elution rate.

Tined leads having tips consisting of porous or molecular sieve-forming material, with a drug being stored in and dispensed from the tip, are disclosed in U.S. Pat. No. 4,819,662, to Heil, Jr. et al.; in U.S. Pat. No. 4,606,118, to Cannon et al.; and in U.S. Pat. No. 4,577,642, to Stokes.

A screw-in pacemaker lead is disclosed in U.S. Pat. No. 4,819,661, to Heil, Jr. et al., which has a chamber open to the distal end of the lead. A matrix impregnated with a therapeutic drug is retained in the chamber. A screw-in lead with a drug impregnated matrix is disclosed in U.S. Pat. No. 4,953,564, to Berthelson, in which the drug elutes out by means of a porous sintered elution path. Because the matrix swells in use, an expansion space is provided.

An implantable, porous stimulating electrode with a thin coating of hydrophilic polymer in which is embedded an anti-inflammatory steroid is disclosed in U.S. Pat. No. 5,103,837, to Weidlich. In this system, the steroid simply diffuses from the polymeric layer into the adjoining tissue to reduce growth of connective tissue.

U.S. Pat. No. 4,711,251, to Stokes, mentioned above, includes an embodiment that uses an osmotic pump to control dispensing of the drug. It has two chambers separated from each other by an impermeable membrane. The inner chamber contains the drug and is adjacent the electrode; the outer chamber is separated from body fluids by a semipermeable membrane. According to the specification, body fluids will enter the outer chamber through the semipermeable membrane to impart a pressure on the inner chamber via the impermeable membrane, resulting in dispensing of the drug stored within the inner chamber through the electrode. However, it is unclear why body fluids would enter the outer chamber to the extent that pressure would be imparted to the inner chamber. Stokes does not describe anything within the outer chamber that would draw in fluid. A figure shows a fluid in the outer chamber; presumably, this is body fluid which has entered the outer chamber after implantation, since no other outer chamber fluid is mentioned.

SUMMARY OF THE INVENTION

The present invention provides a means for controllably releasing one or more drugs from an implantable lead. Both acceleration and deceleration of drug elution may be desired throughout the use of the lead. In a preferred embodiment, a pacing lead has a reservoir containing a polymeric matrix carrying an agent capable of drawing in body fluid, and a second polymeric matrix carrying a drug in powdered form. Moisture from body fluids swells the drawing agent-impregnated material and hydrates the powdered drug. The swollen drawing agent-impregnated material exerts pressure on the second polymeric matrix, squeezing and delivering the drug. More than one type of drug may be contained in the reservoir, for example steroid, antiarrhythmic, antibiotic, or anticoagulant. The drug may also be in liquid form.

In another embodiment, the drawing agent and drug are impregnated in the same material.

In a further embodiment, a drawing agent contained in a polymeric barrier layer covering the drug is used to delay drug elution. The drawing agent must draw body fluid and begin to dissolve before the drug will become hydrated and begin to elute. In this way, the drug delivery rate is slowed in a controllable manner.

In yet another embodiment, more than one type of drawing agent is used to control elution rate of one or more drugs.

It is thus an object of the present invention to provide a means for controllably releasing one or more drugs from an implantable lead.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION OF THE INVENTION

Figure 1:
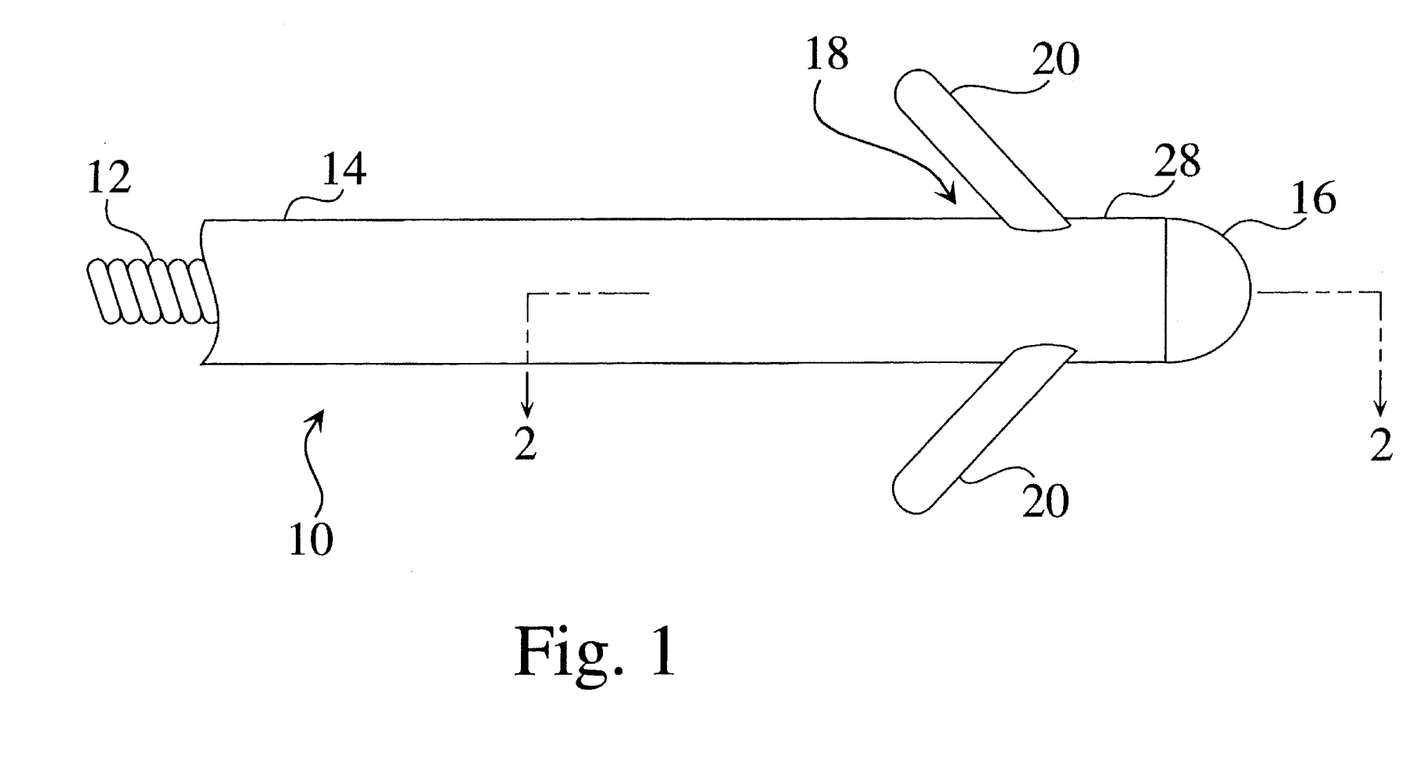
FIG. 1 illustrates a portion of a body implantable lead constructed in accordance with a preferred embodiment of the present invention.

FIG. 1 illustrates a portion of a lead constructed in accordance with the present invention including a lead body 10, formed of a conductor 12 and insulating sheath 14, and a pacing electrode 16. The conductor 12 extends from the pacing electrode 16 to a source of stimulation energy such as an implantable defibrillator, in a known manner. In the illustrated embodiment, the conductor 12 is formed as a helically wound conductor. Alternatively, conductor 12 may be any conductor known in the art. A drug dispenser indicated generally at 18 is carried by the lead and has fixation tines 20 extending therefrom.

Figure 2A:
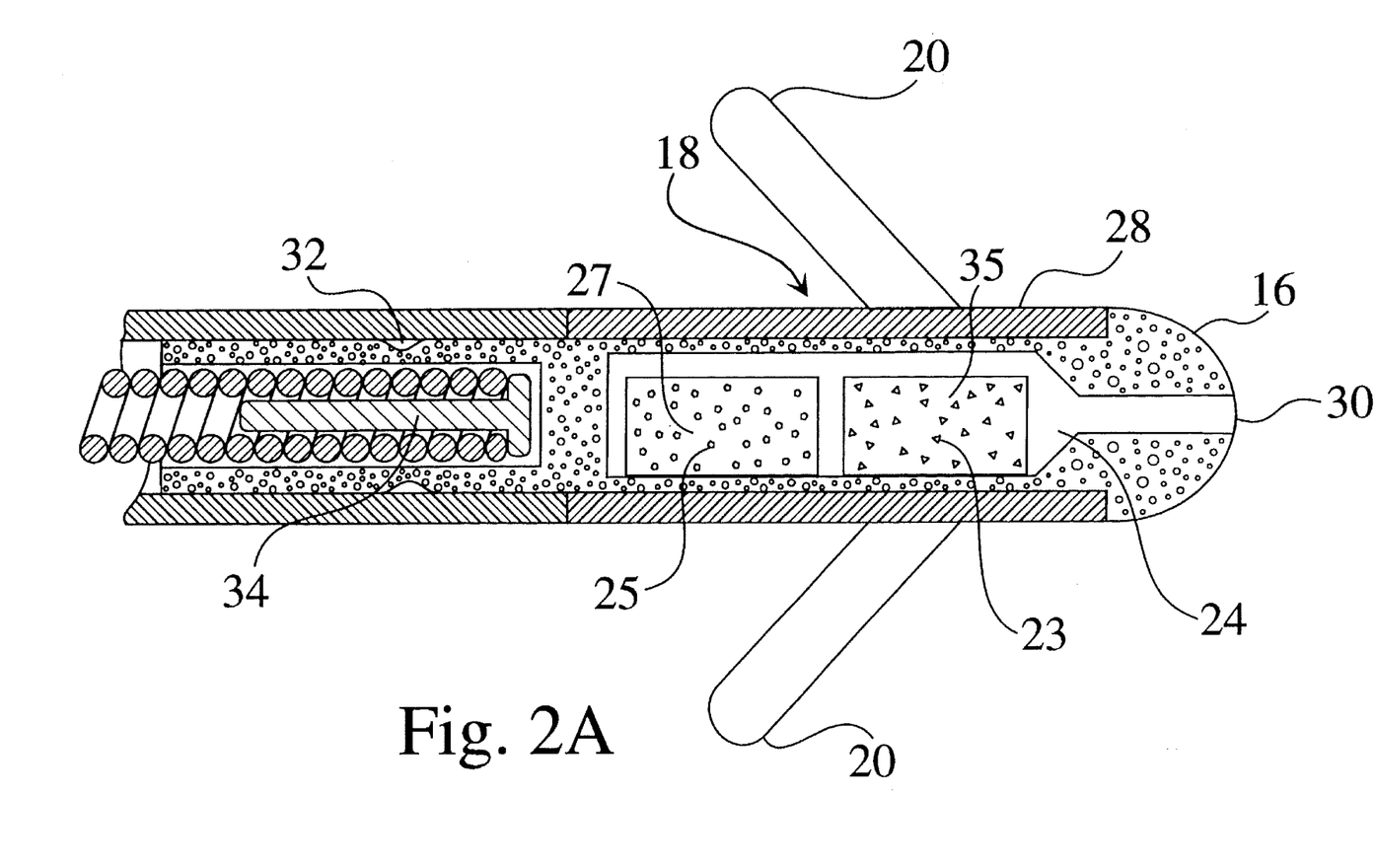
FIGS. 2A, 2B, and 2C illustrate a cross-section taken along the line 2—2 in FIG. 1.

FIG. 2A is a cross-section taken along the line 2—2 in FIG. 1 and illustrates drug dispenser 18 as an osmotic pump. Pump 18 contains a hydrophilic agent 25 impregnated in a polymeric matrix carrier 27 such as silicone rubber. This hydrophilic agent could be a salt or a protein, or a hydrophilic species which is chemically attached to the polymeric matrix, for example. The polymeric matrix may be nondegradable or biodegradable. Likewise, the hydrophilic agent may be nondegradable or biodegradable. An electrically insulating material 28 forms the outer wall of pump 18 while electrode 16 extends to form its inner wall. The electrode 16 is formed of a porous or otherwise permeable, conductive material, and includes a narrow channel 30 extending from the electrode surface to an inner chamber 24, which will be described below. The electrically insulating material 28 may be impermeable or semipermeable, and may be a molded, machined, or extruded polymer, a ceramic, a polymer coating, or a metal oxide, for example. Electrically insulating material 28 may optionally contain or consist of a hydrophilic material, or may be of a structure to increase capillary action, to help draw body fluid into the electrode 16 to speed the hydration rate of the drug and hydrophilic agent 25, thus accelerating drug delivery. Alternatively, the hydrophilic material within the electrically insulating material 28 may be of a high concentration so as to form a barrier which must be hydrated before the hydrophilic agent 25 can be hydrated, thereby decelerating drug delivery.

Electrode 16 is crimped as at 32 to maintain electrical communication between it and the conductor 12. A crimp pin 34 is used to support conductor coil 12 when forming crimp 32 onto electrode 16.

A drug 23 is contained within a second polymeric matrix carrier 35 within chamber 24, and may be any suitable drug intended to accomplish any desirable localized purpose. The second polymeric matrix carrier 35 may be nondegradable or biodegradable. The drug may be one intended to counter thrombus formation, fibrosis, inflammation, or arrhythmias, or any combination of drugs intended to accomplish one or more of those purposes, or any drug or combination of drugs intended to accomplish any other desirable localized purpose or purposes. As an example, the steroid dexamethasone sodium phosphate, would be an appropriate drug for reducing fibrotic growth.

After the lead is implanted, body fluids will enter the chamber 24 through porous electrode 16, channel 30, and semipermeable electrically insulating material 28, hydrating the hydrophilic agent 25, and causing the polymeric matrix carrier 27 to expand to impart a pressure on the drug 23 and its carrier 35. This will result in a dispensing of the drug 23 through electrode 16 and through channel 30. In the case where the drug is a liquid or is in solution, it is dispensed immediately as pressure is applied. If the drug is in powder form, it must become hydrated; as it does so, its expansion will act to further increase the rate of drug elution, or dispensing. Note that not all three fluid paths described must be present for this invention to work. Some possible combinations are: 1) electrode 16 is nonporous, insulating material 28 is impermeable, and electrode 16 includes a channel 30; 2) electrode 16 is porous, insulating material 28 is impermeable, and electrode 16 includes a channel 30; 3) electrode 16 is porous, insulating material 28 is permeable, and channel 30 may or may not be included in electrode 16; 4) electrode 16 is porous but does not include a channel, and insulating material 28 is impermeable; and 5) electrode 16 is nonporous and includes a channel 30, and insulating material 28 is permeable. These various combinations allow control of drug outflow direction and duration.

The degree of swelling is controlled in part by the type and concentration of the hydrophilic agent 25. Also, if the hydrophilic agent is a protein, to increase hydration rate, the pore size of the semipermeable insulating material 28 and electrode 16 can be larger than for a salt, since the larger protein molecules will not pass through. The degree of swelling could also be varied with polymeric matrix crosslink density of both the polymeric matrix holding the hydrophilic agent, and that holding the drug. That is, for a highly crosslinked polymer, the degree of swelling is likely to be lower than for a polymer that is less crosslinked. Hydrophilicity of the salt or protein may also be used to vary the rate or extent of swelling. The final amount of swelling could be varied with both crosslink density and hydrophilic agent content or hydrophilicity.

Figure 2B:
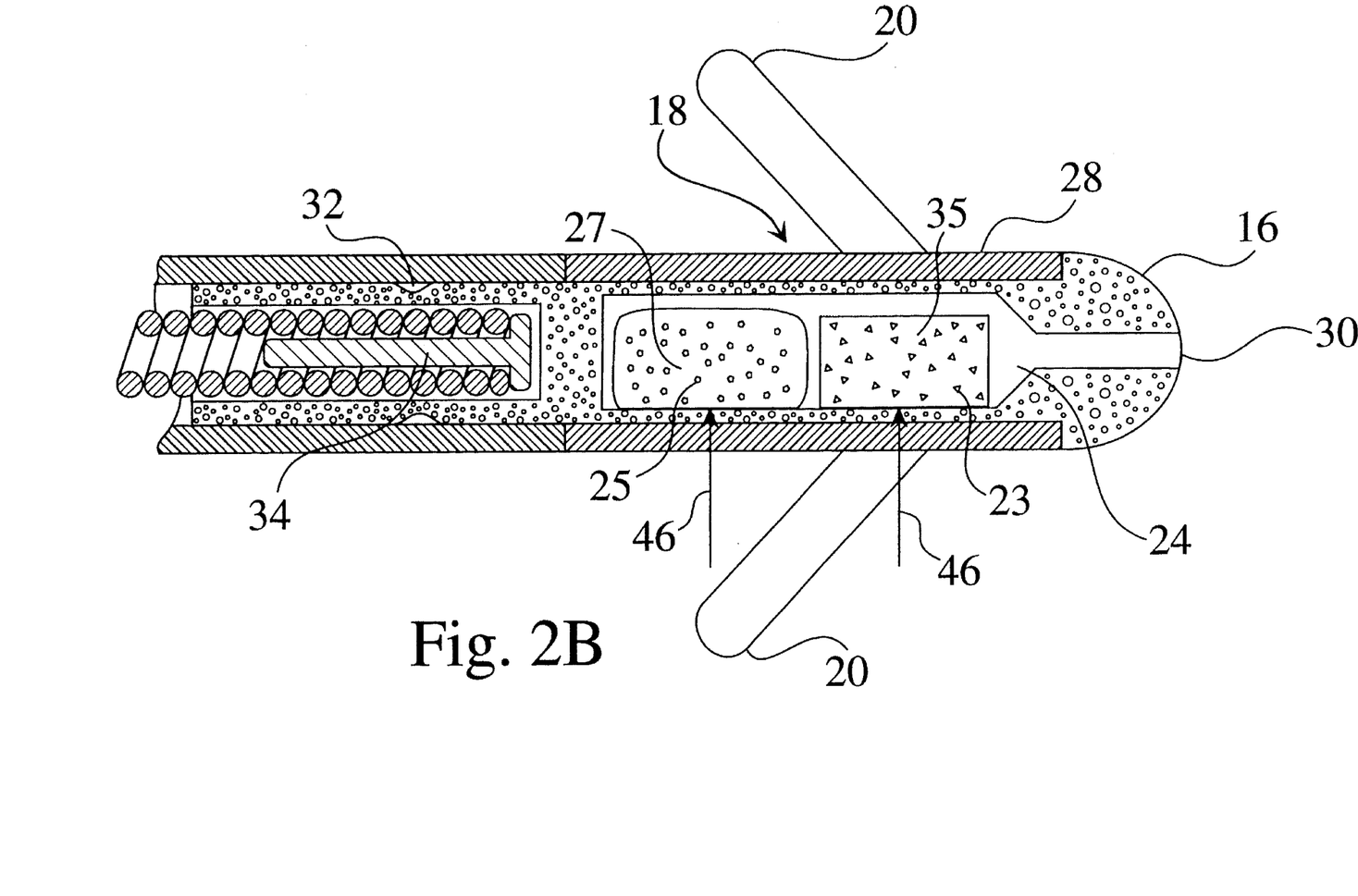
Figure 2C:
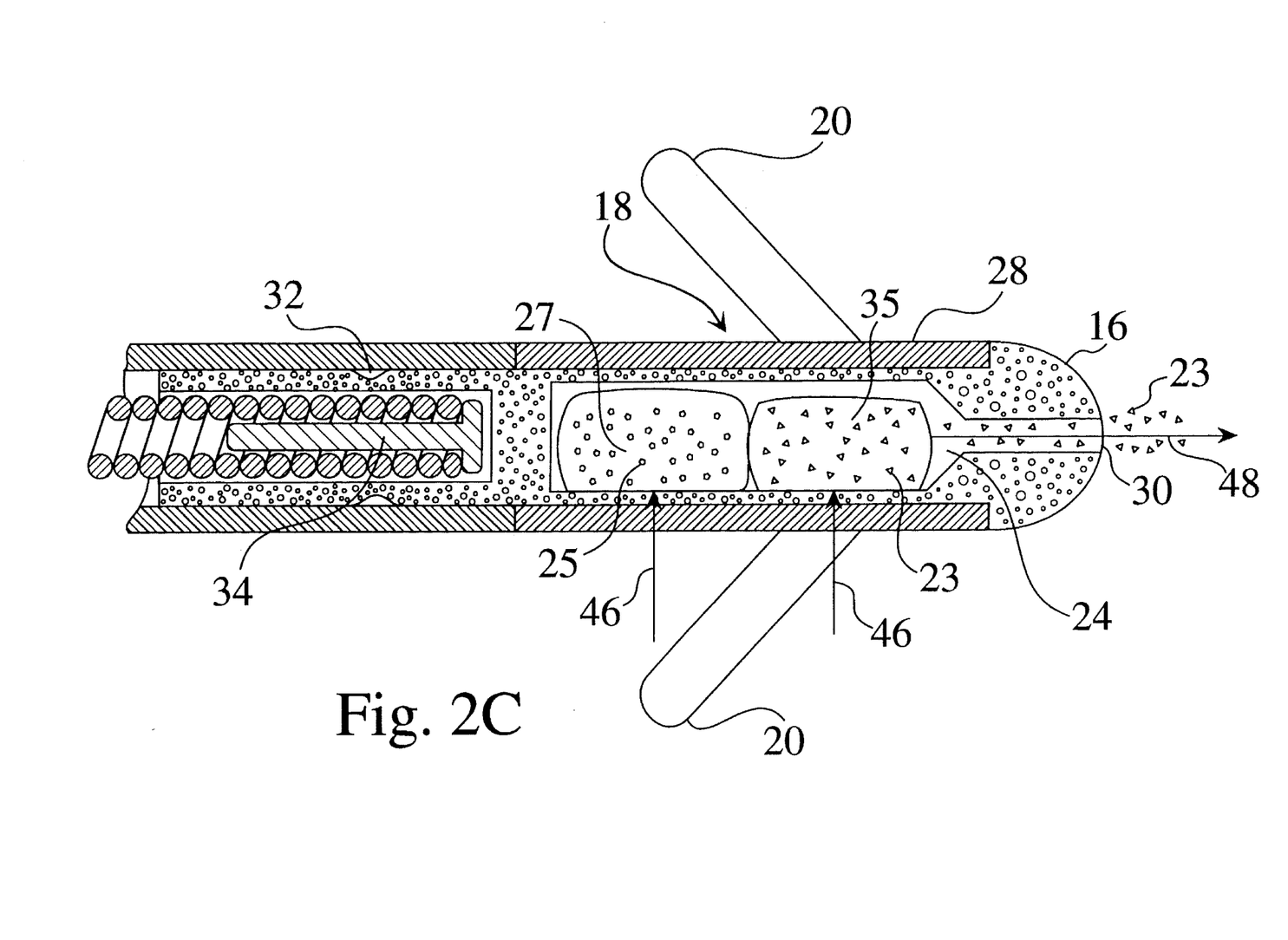

FIGS. 2B and 2C show body fluid being drawn (arrows 46) into the drug to solvate the drug, and into the fluid drawing agent to swell it and squeeze on the drug carrier to dispense it to the body (arrow 48).

Figure 3A:
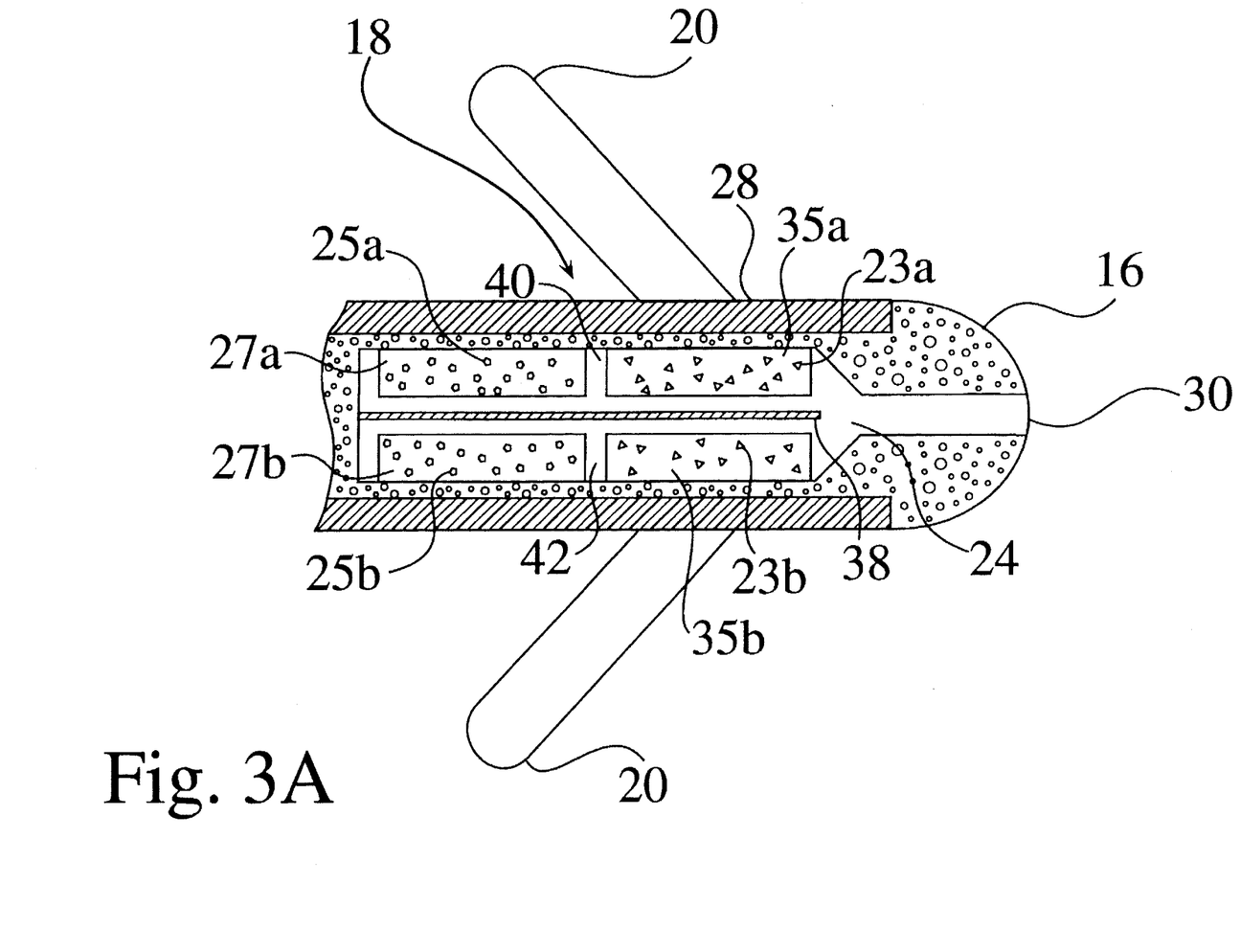
FIGS. 3A and 3B are cross-sectional views of leads having more than one drug and more than one type of drawing agent to control elution rate.
Figure 3B:
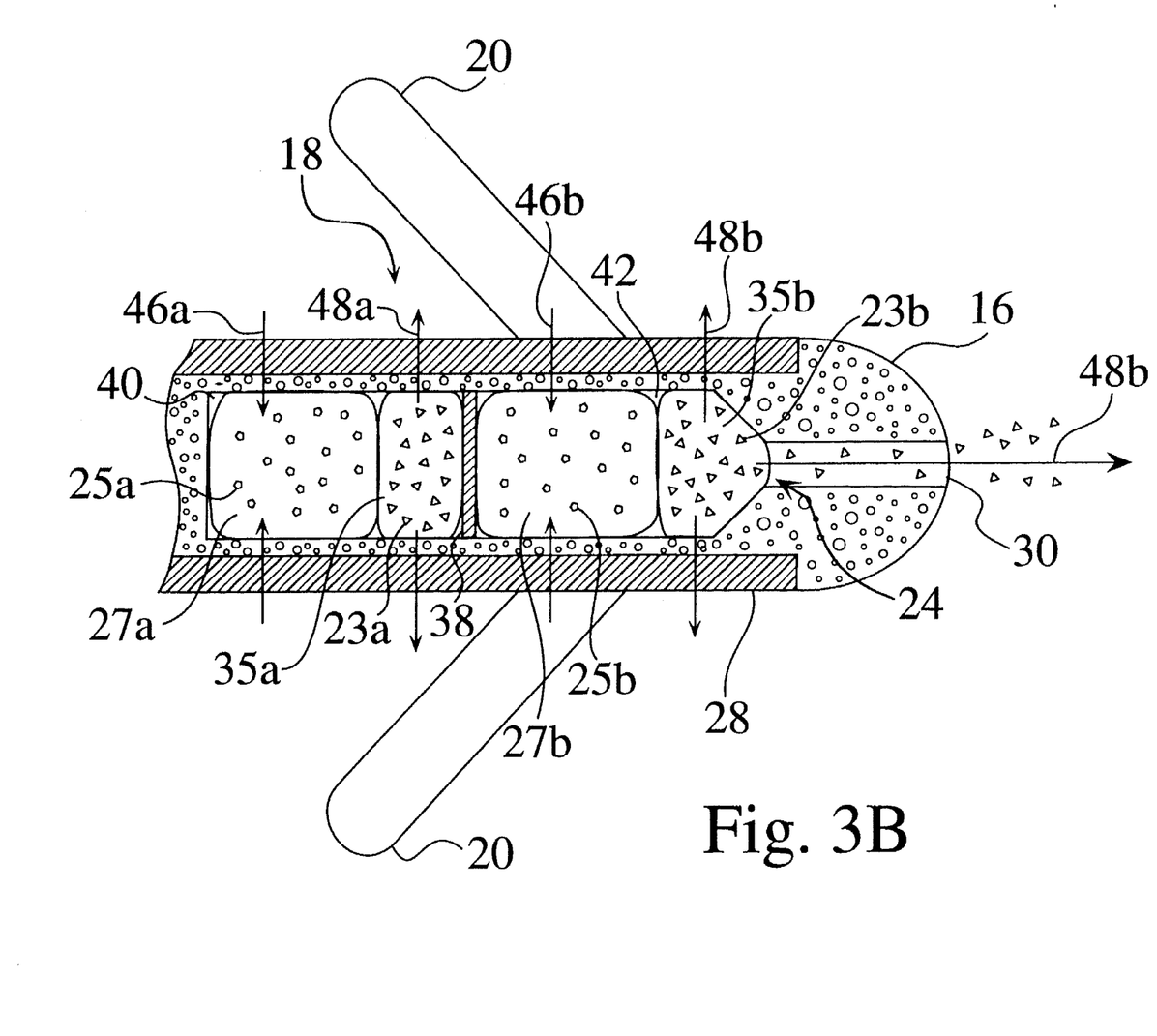

FIGS. 3A and 3B show leads having more than one type of salt 25a and 25b for drug elution rate control within polymeric matrix carriers 27a and 27b. Matrix carriers 27a and 27b may be the same or different polymers. Also, several different drugs 23a and 23b may be used in combination within carriers 35a and 35b, which also may be the same or different. Drug 23a and salt 25a are shown to be separated from drug 23b and salt 25b by a separator 38, which also divides larger chamber 24 into two smaller chambers 40 and 42. Each drug may be impregnated in a different matrix in an appropriate concentration to achieve its desired elution rate. Several pumping elements that swell and pump differently may be used to control the elution rate of the drugs. Arrows in FIG. 3B show the direction of fluid flow; body fluids enter chambers 40 and 42 to swell salts 25a and 25b (arrows 46a and 46b), and hydrated drugs 23a and 23b elute into the patient's body (arrows 48a and 48b). Note that in the case of FIG. 3B having separator 38, insulating material 28 and electrode 16 must be permeable to both the body fluid and the drug in the area behind the separator, since otherwise, drug 23a could not elute into the patient's body as shown by arrow 48a. In most of the other embodiments presented herein, it is desirable that the electrically insulating material 28 not be permeable to the drug 23 so that direction of drug dispensing is controlled and is confined to the channel 30, or to the tip of porous electrode 16, or both. By making the insulating material 28 and electrode 16 permeable to water only, hydration rate is increased without concern for direction of water ingress, but drug dispensing direction is controlled.

Figure 4:
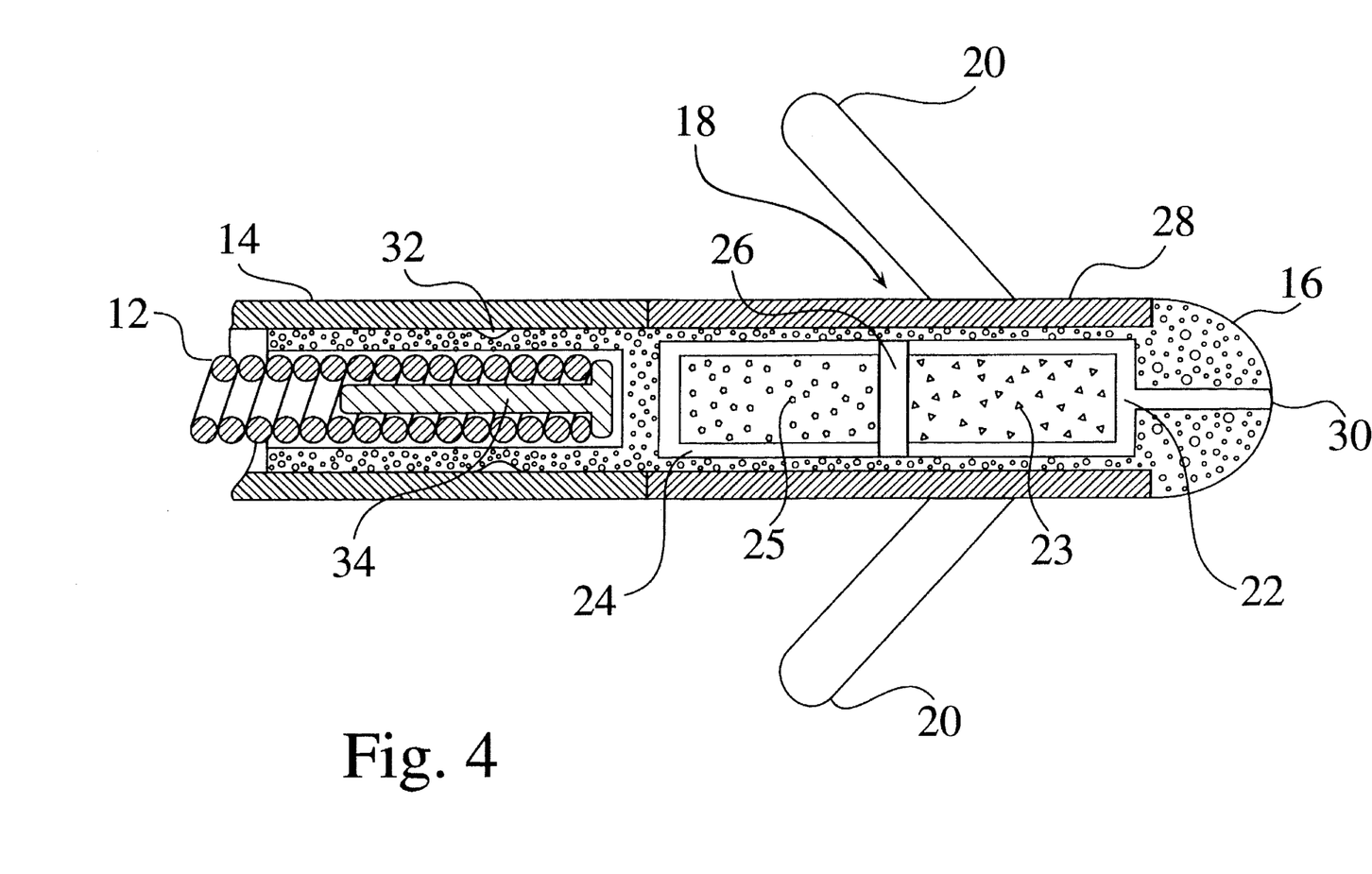
FIG. 4 is a cross-sectional view of another embodiment of the invention.

FIG. 4 illustrates drug dispenser 18 in cross section as an osmotic pump. Pump 18 has outer and inner chambers 22 and 24, respectively, separated by an impermeable membrane 26. A semipermeable electrically insulating material 28 forms the outer wall of chambers 22 and 24 while electrode 16 extends to form the inner wall of chambers 22 and 24. The electrode 16 is formed of a porous, conductive material, and includes a channel 30 from the outer chamber 22 to the patient's body. Chamber 24 contains a hydrophilic agent 25 which may be in powder form, in the form of a hypertonic solution, or impregnated in a polymeric matrix such as silicone rubber. This hydrophilic agent may be a salt or a protein, for example.

Prior to implantation, the chamber 22 is charged with a drug 23 to be dispensed. The drug may be in powder form, in solution, or impregnated in a polymeric matrix, and may be any suitable drug intended to accomplish any desirable localized purpose. After the lead is implanted, body fluids will enter the chamber 24 through the semipermeable electrically insulating material 28 and porous electrode 16, hydrating the hydrophilic agent, and causing it to press against impermeable membrane 26, thus increasing the pressure in chamber 22. This will result in a dispensing of the drug stored within chamber 22 through channel 30, electrode 16, and semipermeable electrically insulating material 28, at a rate which depends on their presence, porosity, and permeability, respectively. If the drug is a liquid or is in solution, it can be dispensed immediately as pressure is applied by the impermeable membrane. If the drug is in powder form, it must become hydrated; as it does so, the volume increase will act to further increase the rate of drug dispensing.

Figure 5:
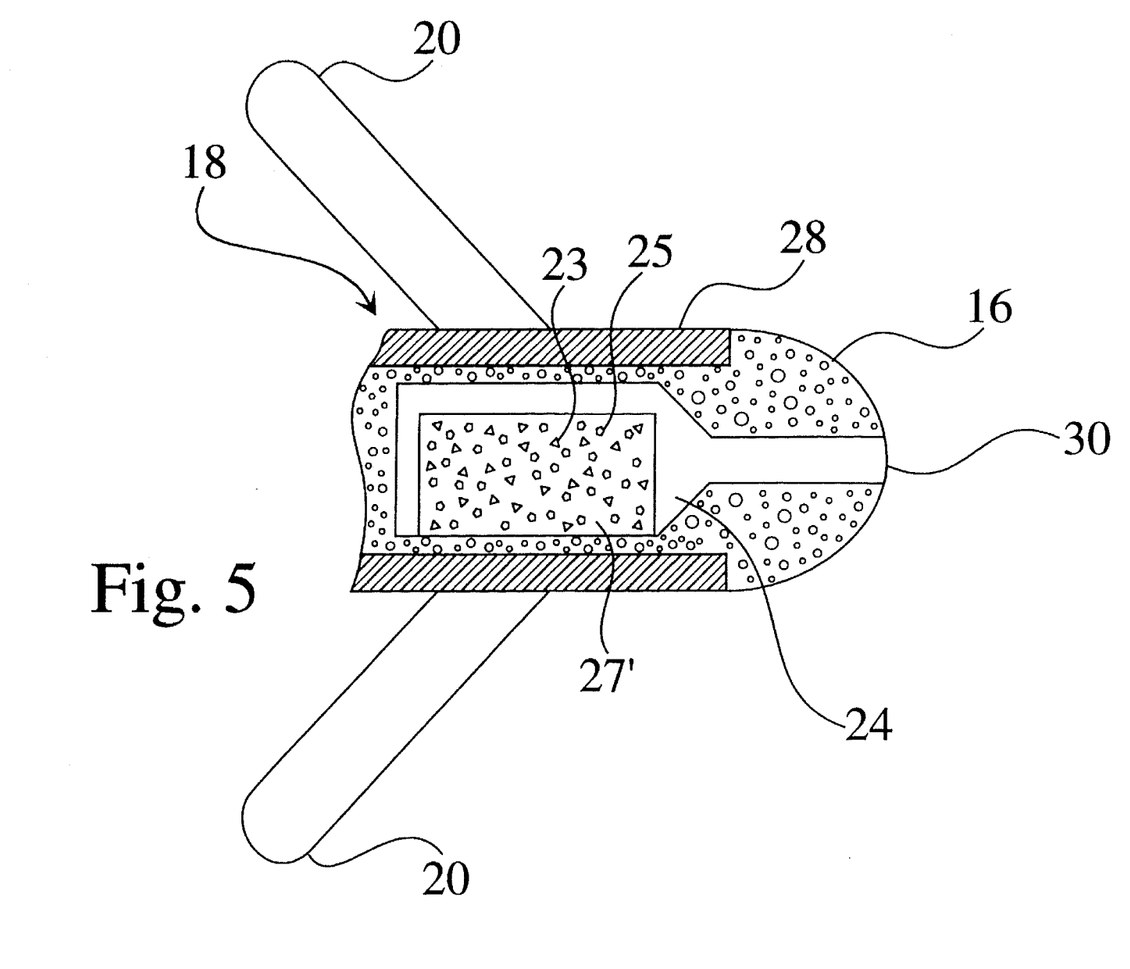
FIG. 5 is a cross-sectional view of another embodiment of the invention in which a drug and drawing agent are embedded in the same polymeric matrix.

FIG. 5 shows an osmotic pump 18 having a drug 23 and a hydrophilic agent 25 mixed into the same polymeric matrix 27'. This would work in a similar manner as the pump of FIG. 2, except that the pumping would occur not only from back of chamber 24 to the patient's body, but from every part of the chamber 24 to the patient's body.

Figure 6A:
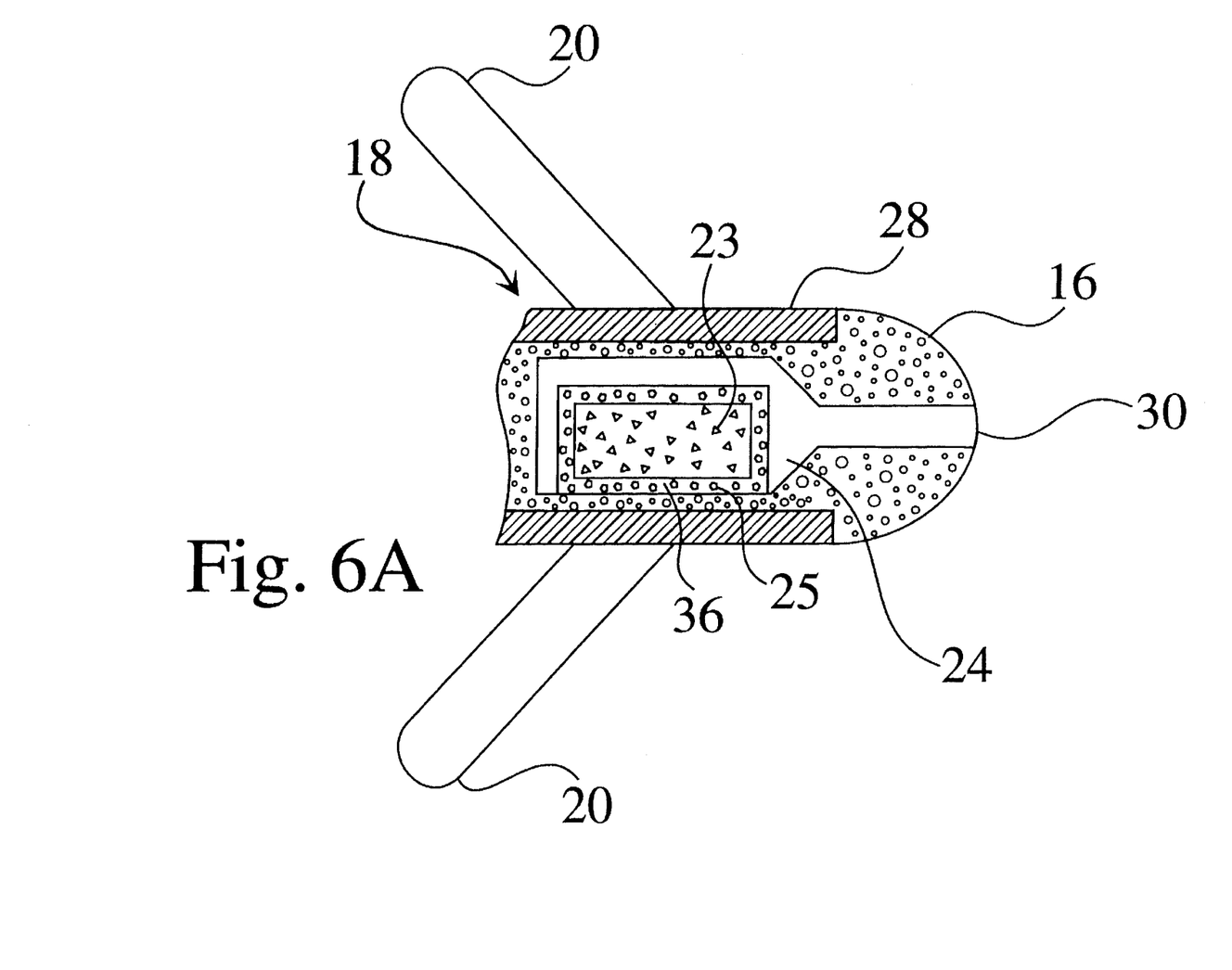
FIGS. 6A, 6B, and 6C are cross-sectional views of another embodiment of the invention in which a drawing agent barrier is used to delay drug elution.
Figure 6B:
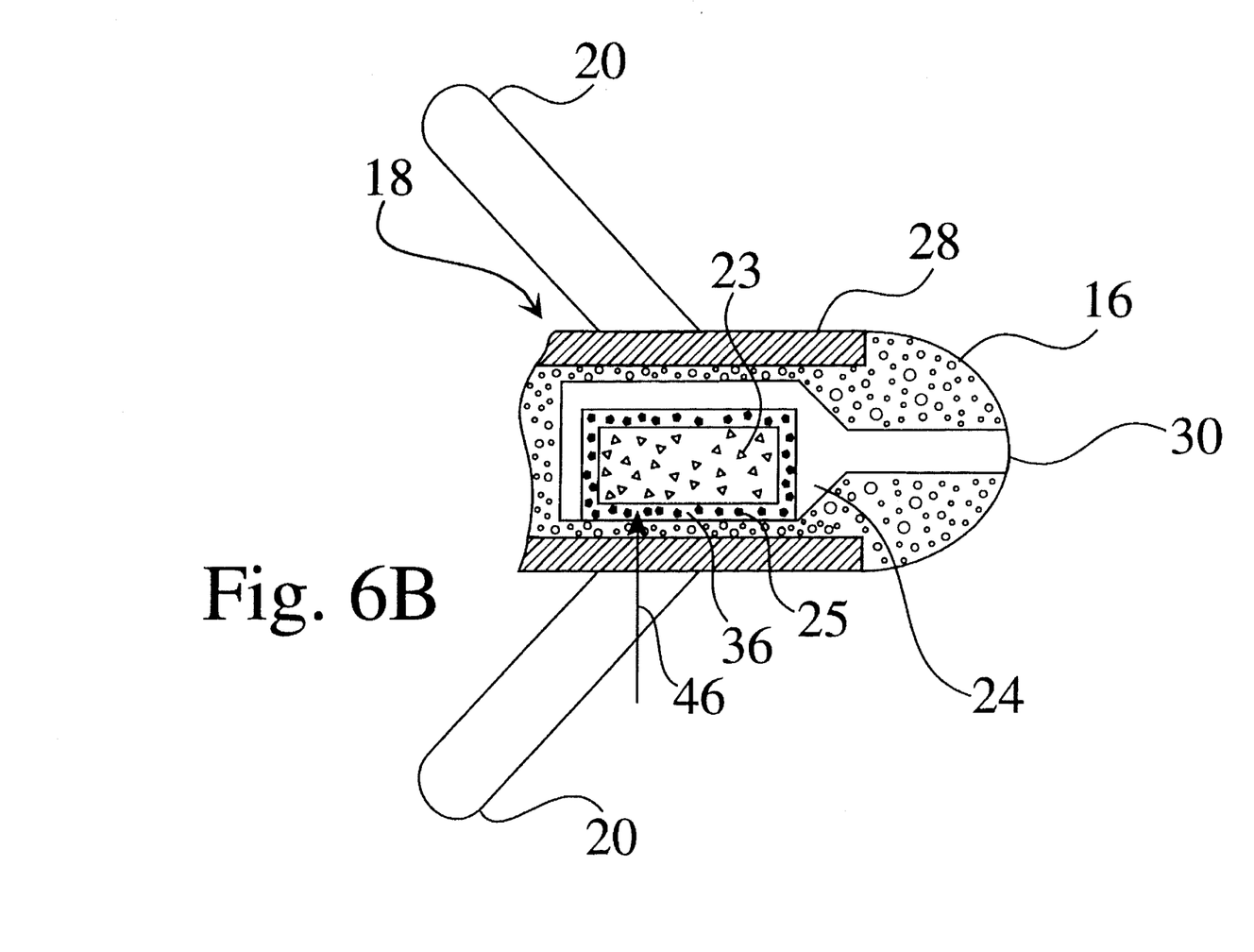
Figure 6C:
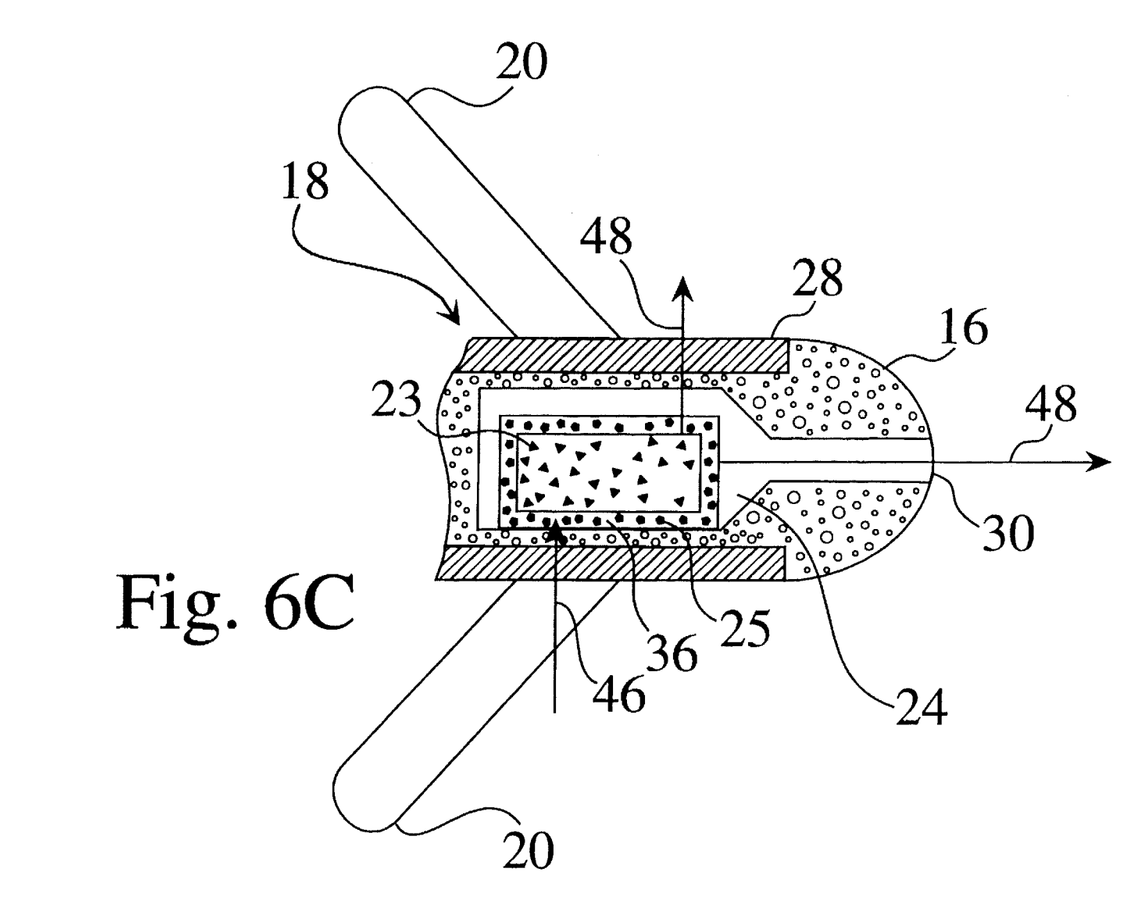

FIG. 6A shows an osmotic pump 18 having a barrier layer 36 containing salt 25 which must be hydrated first before drug 23 can be hydrated to begin elution. Salt 25 may be embedded in a polymeric matrix that is permeable to drug 23 when hydrated, or may be in crystalline form, to form the covering 36 on drug 23. Likewise, drug 23 may be only drug, or may be embedded in a polymeric matrix. It also may be embedded in the matrix along with more of salt 25 or a different hydrophilic agent, in the manner described with reference to FIG. 5. In FIG. 6B, water enters barrier layer 36 (arrow 46), preferentially binding with salt 25, initially preventing hydration of drug 23. In FIG. 6C, salt 25 has become hydrated to the point where water begins to dissolve drug 23, allowing drug 23 to begin eluting (arrow 48) to the body.

Figure 7A:
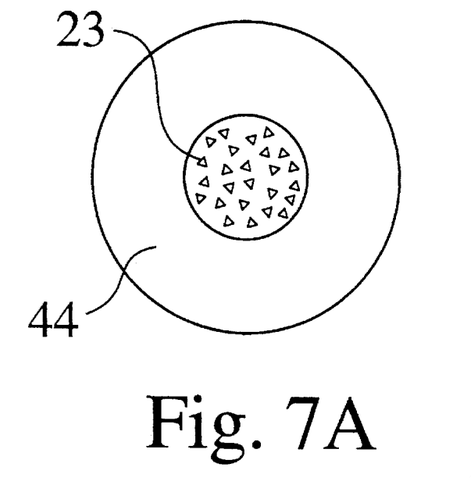
FIGS. 7A, 7B, and 7C illustrate a drawing agent surrounding a drug, swelling with body fluid, and bursting to release the drug.
Figure 7B:
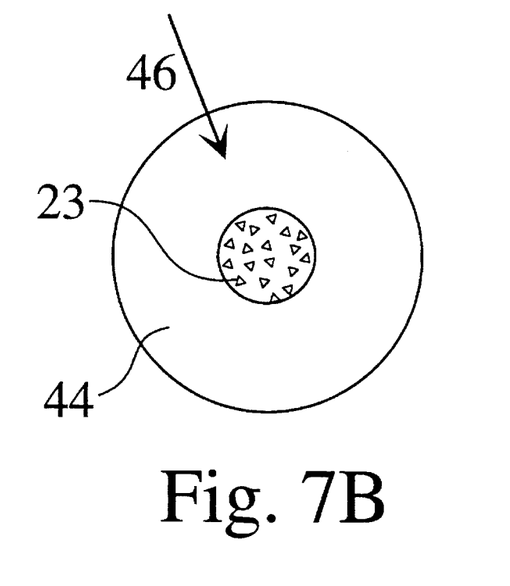
Figure 7C:
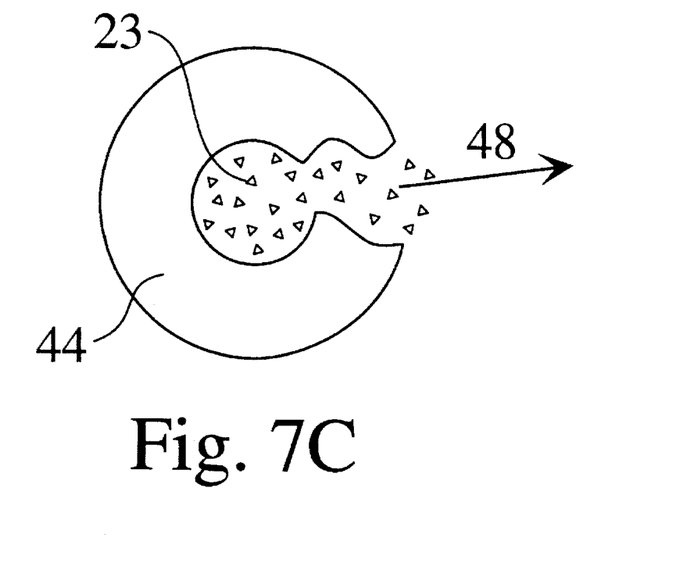

FIG. 7A shows a drug 23 in liquid or powder form surrounded by a salt filled polymer 44. In FIG. 7B, body fluid swells the salt filled polymer 44 (arrow 46), until the salt filled polymer 44 fractures to release the drug 23 (arrow 48), as shown in FIG. 7C.

Note that fracture of the polymer is not required for drug delivery to be delayed. The salt barrier can act as a water "getter" until it is at equilibrium hydration, as described in FIGS. 6A, 6B, and 6C.

As an example of delaying drug delivery by this invention, consider a drug that is desired to be delivered only after the electrode is encapsulated within a vessel or affixed to a cardiac wall. To prevent the drug from leaking out earlier, then providing for slow drug delivery, a salt would be used that is of appropriate solvating power to delay hydration of the drug long enough to prevent delivery of the drug until tissue ingrowth occurs. The hydration of the drug in the inner matrix activates drug elution, so by inhibiting or slowing hydration of the inner rubber matrix, drug elution will be limited.

In the embodiments of the invention presented above, a hydrophilic agent is used to regulate drug elution. However, because the body contains fluids having both polar components, like water, and nonpolar components, like fatty acids, a lipophilic agent could be used in place of a hydrophilic agent in many of the above embodiments, with very little modification. For example, silicone rubber generally swells much more in nonpolar solvents than in water, and may be more affected by the fatty acids than by the water in the blood. In the case of FIGS. 7A, 7B, and 7C, for example, a mechanically weak lipophilic outer covering may be used instead of salt filled polymer 44 to surround the drug 23; the lipophilic outer covering would swell from the nonpolar substances in the blood, then burst to release the drug. In other figures described above, hydration of the hydrophilic agent and subsequent hydration of the drug was used to deliver the drug; in some cases, the drug was hydrophilic and hydration of the drug was necessary to draw it out of the electrode and into the body. However, if the drug is lipophilic or has a lipophilic portion, and thus dissolves in lipids, a lipophilic agent may be used instead of a hydrophilic agent to draw in nonpolar blood substances that will then be used to dissolve the drug into the blood. Dexamethasone is an example of a lipid soluble drug. The blood lipids include free fatty acids, diglycerides, triglycerides, phospholipids, sterols, carotenoids, fat-soluble vitamins, hydrocarbons, and prostaglandins. The electrode position is not limited to the blood, and may be in a location in the body with a much higher concentration of lipids. As another example of using this invention, in FIG. 4, drawing agent 25 may be hydrophilic, drawing in water from blood through semipermeable insulation 28 and porous electrode 16 to expand and press on impermeable membrane 26; drug 23 may be lipophilic, drawing in blood and dissolving into the fatty acid portions of the blood, and is then squeezed out of the electrode through channel 30 by the pressure of hydrated agent 25.

The above has been offered for illustrative purposes only and is not intended to limit the scope of the invention of this application, which is as defined in the claims below.

That which is claimed is:

1. An implantable device, comprising:
    an electrode for implantation in a patient, said electrode having a reservoir located within said electrode;
    an insulated conductor having a distal end and a proximal end and coupled to said electrode at said distal end of said conductor and having a connector at said proximal end of said conductor;
    at least one therapeutic drug carried in said reservoir; and
    at least one drawing agent contained in said reservoir, having an ability to draw body fluid into said reservoir for modulating drug delivery rate of said at least one therapeutic drug to body tissue.

2. The implantable device of claim 1, wherein said agent is hydrophilic.

3. The implantable device of claim 1, wherein said agent is lipophilic.

4. The implantable device of claim 1, wherein more than one said agent is contained in said reservoir to provide different pumping effects.

5. The implantable device of claim 2 wherein said hydrophilic agent is a salt.

6. The implantable device of claim 2 wherein said hydrophilic agent is a protein.

7. The implantable device of claim 1 and further including a polymeric matrix within said reservoir, wherein said drawing agent is impregnated in said polymeric matrix.

8. The implantable device of claim 7 wherein said polymeric matrix is biodegradable.

9. The implantable device of claim 2 and further including a polymeric matrix within said reservoir, wherein said hydrophilic agent comprises a hydrophilic species chemically attached to said polymeric matrix.

10. The implantable device of claim 1 and further including a polymeric matrix within said reservoir, wherein said therapeutic drug is impregnated in said polymeric matrix.

11. The implantable device of claim 9 wherein said polymeric matrix is biodegradable.

12. The implantable device of claim 1 wherein said therapeutic drug is in liquid form.

13. The implantable device of claim 1, wherein said drawing agent is impregnated in a first polymeric matrix, and said therapeutic drug is impregnated in a second polymeric matrix, and said drug and said drawing agent are separated by an impermeable membrane, said first polymeric matrix expanding upon solvation of said drawing agent to press on said drug and said second polymeric matrix with said impermeable membrane, causing said drug to be dispensed.

14. The implantable device of claim 1 wherein said drug and said drawing agent are mixed together into a polymeric matrix.

15. The implantable device of claim 1, and further comprising a barrier layer containing a drawing agent which must be dissolved before said drug can be dissolved to begin elution.

16. A pump for dispensing a therapeutic drug to a patient's body, comprising:
   a chamber containing a polymeric matrix, a therapeutic drug, and a hydrophilic agent, wherein said hydrophilic agent is embedded in said polymeric matrix;
   an electrically insulating material forming an outer wall of said chamber; and
   an electrode forming an inner wall of said chamber.

17. The pump of claim 16 wherein said electrode has a channel from said chamber to said patient's body.

18. A body implantable lead comprising:
   an electrode for sensing or stimulation for implantation in a patient's body;
   an insulated conductor having a distal end and a proximal end and coupled to said electrode at said distal end of said conductor and having a connector at said proximal end of said conductor; and
   a drug eluting system located within said electrode having at least one therapeutic drug and at least one fluid drawing agent for use as a pump for delivering said at least one therapeutic drug to tissue.

19. The lead of claim 18, wherein said drug eluting system has a plurality of fluid drawing agents to provide different pumping effects.

20. The lead of claim 18 wherein said fluid drawing agent is lipophilic.

21. The body implantable lead of claim 18 and further comprising a polymeric matrix within said electrode, wherein said fluid drawing agent is impregnated in said polymeric matrix.

22. The lead of claim 18 and further comprising a polymeric matrix within said electrode, wherein said therapeutic drug is impregnated in said polymeric matrix.

23. The lead of claim 22 wherein said polymeric matrix is biodegradable.

24. The lead of claim 18 wherein said therapeutic drug and said fluid drawing agent are separated by an impermeable membrane, said fluid drawing agent expanding upon drawing of fluid to press on said drug with said impermeable membrane, causing said drug to be dispensed.

25. The lead of claim 18, and further comprising a chamber containing said drug and a fluid drawing agent which is embedded in a polymeric matrix, said chamber having an electrically insulating material forming an outer wall and said electrode forming an inner wall.

26. The lead of claim 25 wherein said electrode has a channel from said chamber to the patient's body,.

27. The lead of claim 25 wherein said electrically insulating material is semipermeable.

28. A drug eluting system for use in an implantable electrode comprising:
   a porous electrode;
   an outer chamber formed by a semipermeable electrically insulating material and containing at least one therapeutic drug;
   an inner chamber formed by a semipermeable membrane and containing a hydrophilic agent for use as an osmotic pump for delivering said at least one therapeutic drug to tissue;
   an impermeable membrane separating said outer chamber from said inner chamber, said semipermeable membrane allowing body fluid to pass through to said inner chamber, said hydrophilic agent expanding upon hydration to press on said drug with said impermeable membrane, causing said drug to be dispensed through said semipermeable electrically insulating material and through said porous electrode.

* * * * *